United States Patent [19]
Sepetka et al.

[11] Patent Number: 5,843,118
[45] Date of Patent: Dec. 1, 1998

[54] FIBERED MICRO VASO-OCCLUSIVE DEVICES

[75] Inventors: Ivan Sepetka, Los Altos; Son M. Gia, San Jose, both of Calif.

[73] Assignee: Target Therapeutics, Inc., Fremont, Calif.

[21] Appl. No.: 807,194

[22] Filed: Feb. 27, 1997

Related U.S. Application Data

[63] Continuation of Ser. No. 566,608, Dec. 4, 1995, abandoned.

[51] Int. Cl.$^6$ .................................................. A61M 29/00
[52] U.S. Cl. ......................... 606/194; 606/191; 606/198; 606/200; 623/1; 623/11
[58] Field of Search .................................... 606/191, 194, 606/198, 200; 604/104; 623/1, 11

[56] References Cited

U.S. PATENT DOCUMENTS

| | | | |
|---|---|---|---|
| 4,739,768 | 4/1988 | Engelson | 604/282 |
| 4,823,794 | 4/1989 | Pierce | 606/232 |
| 4,994,069 | 2/1991 | Ritchart et al. . | |
| 5,095,917 | 3/1992 | Vancaillie . | |
| 5,123,914 | 6/1992 | Cope | 606/232 |
| 5,192,301 | 3/1993 | Kamiya et al. . | |
| 5,203,787 | 4/1993 | Noblitt et al. | 606/232 |
| 5,226,911 | 7/1993 | Chee et al. . | |
| 5,304,194 | 4/1994 | Chee et al. . | |
| 5,370,657 | 12/1994 | Irie | 606/200 |
| 5,382,259 | 1/1995 | Phelps et al. . | |
| 5,443,478 | 8/1995 | Purdy . | |
| 5,462,523 | 10/1995 | Samson et al. | 604/280 |
| 5,527,338 | 6/1996 | Purdy | 606/200 |
| 5,549,624 | 8/1996 | Mirigian et al. | 606/191 |
| 5,634,942 | 6/1997 | Chevillon et al. | 606/200 |

FOREIGN PATENT DOCUMENTS

| | | |
|---|---|---|
| 2 608 418 | 6/1988 | France . |
| 4-312454 | 4/1992 | Japan . |
| WO 94/10936 | 5/1994 | WIPO . |

*Primary Examiner*—Michael Powell Buiz
*Assistant Examiner*—Daphna Shai
*Attorney, Agent, or Firm*—Morrison & Foerster LLP

[57] ABSTRACT

This is a micro-vaso-occlusive device intended generally for occlusion of small arteries located distally in the vasculature. The invention is made up of a binder portion, often radio-opaque, which is short in length in comparison to the length of the included thrombogenic fibers. The fibers from the other portion of the device. The micro device may have multiple binder sections. The fibers may be straight, looped, or tufted.

17 Claims, 6 Drawing Sheets

FIBERED MICRO VASO-OCCLUSIVE DEVICES

This is a continuation of application Ser. No. 08/566,608 filed Dec. 4, 1995, now abandoned.

FIELD OF THE INVENTION

This invention is a surgical device. In particular, it is a micro-vaso-occlusive device intended generally for occlusion of small arteries located distally in the vasculature. The invention is made up of a binder, often radio-opaque, which is short in length in comparison to the length of the included thrombogenic fibers. The fibers from the other portion of the device. The micro device may have multiple binder section. The fibers may be straight, looped, or tufted.

BACKGROUND OF THE INVENTION

The use of occlusive devices in the vascular system and in other systems of the body, e.g., genito-urinary and biliary systems, is known. In the vasculature, a physician may apply a vaso-occlusive device using endovascular techniques to a selected site to cause the site to fill with thrombus. The occlusion often changes in composition to a more collagenous composition over time.

A variety of maladies may be treated in this way. For instance, an occlusion may be used to limit bleeding due to vascular accidents such as strokes or to fill abnormal vascular cavities such as aneurysm or to limit the flow of blood to an anomalous anatomical region, e.g., a tumor or one of the extraneous sites in a multifocal electrical arrhythmia.

Occlusive devices and materials used in such service are typically of two types: solids and reactive fluids. The class of solid-occlusive devices includes an eclectic variety of materials: hog hair, polyvinyl alcohol beads, collagen beads, latex beads, and silk or rayon fibers. Devices such as coils or balloons are also known and used.

Cyanoacrylate glues are occasionally applied as vaso-occluding materials. These are not type-approved and a specific approval must be determined for each use. Glues are difficult to place within the vasculature and although they create excellent occlusions, they may do so at a site downstream of the desired site.

The most practical of these devices and methods from both a precision placement aspect and an effectiveness aspect are vaso-occlusive coils with or without added thrombogenic fibers. An early endovascular coil device is found in Ritchart, et al., U.S. Pat. No. 4,994,069. These devices are lengthy in comparison to the inventive devices described here and rely on the volume of the coil and the secondary shape of the coil after it exits the delivery catheter for defining the bulk of the resulting occlusion.

A variation of the vaso-occlusive coils are shown in U.S. Pat. Nos. 5,226,911 and 5,304,194 to Chee et. al. Those patents show the use of longer vaso-occlusive coils having attached fibrous elements which are looped from place-to-place along the coils.

A further variation is shown in U.S. Pat. No. 5,382,259, to Phelps et. al. Phelps et al. shows a coil having a braided fibrous covering on the exterior of the coil. The braid is placed on the coil for the purpose of increasing the assembly's tendency to produce thrombus.

None of these devices are vaso-occlusive devices having short binders holding significantly longer fibers.

Other occluding devices having a plug-like form are known.

U.S. Pat. No. 5,095,917, to Vancaille, shows a transuterine technique for sterilization of females using a biodegradable plug. The plug is used in conjunction with the destruction of a mucous layer to form a site for inflammation and, upon healing, form an occlusion. No fibers are used in conjunction with the plug.

U.S. Pat. No. 5,192,301, to Kamiya et al., shows a closing plug which is to be delivered percutaneously to close somatic wall defects such as arterial septal defects (ASD). The plug is preferably of a shape memory polymer and has shape involving a cone at one end and a flange at the other. Again, fibers are not involved in the structure of the device.

U.S. Pat. No. 5,443,478, to Purdy, shows a multi-element vascular device having an anchoring element and a lead element connected by fibers. The anchoring element is typically a coil forming a circular element. After deployment of the device from a delivery catheter, the anchoring element secondary shape is approximately the size of the vessel to be occluded. The typically somewhat smaller lead element is also often a coil but is depicted to be of a smaller size than the anchoring element. The fibers are not aligned with the coil upon deployment of the device, however.

Japanese Kokai 4-312454 shows an occlusive device which appears to have multiple magnetic portions. The magnetic portions are shown to be square in FIG. 1 and spherical in FIG. 3 of the publication. The magnetic portions do not appear to act as clasps on the fiber.

None of the disclosed devices are similar to the inventive vaso-occlusive device.

SUMMARY OF THE INVENTION

This is a vaso-occlusive device made up of at least one short retainer and a longer fiber bundle. The retainer may be radio-opaque. The fibers may be straight, looped, or tufted. The primary use of the device is in the very small vessels at the distal portion of the vasculature.

DESCRIPTION OF THE INVENTION

The invention is a vaso-occlusive device typically made up of two components (which may be used in multiples): a retainer and a multiplicity of thrombogenic fibers, often in the form of a bundle. The retainer may also include a clip for fibers.

Figure 1:
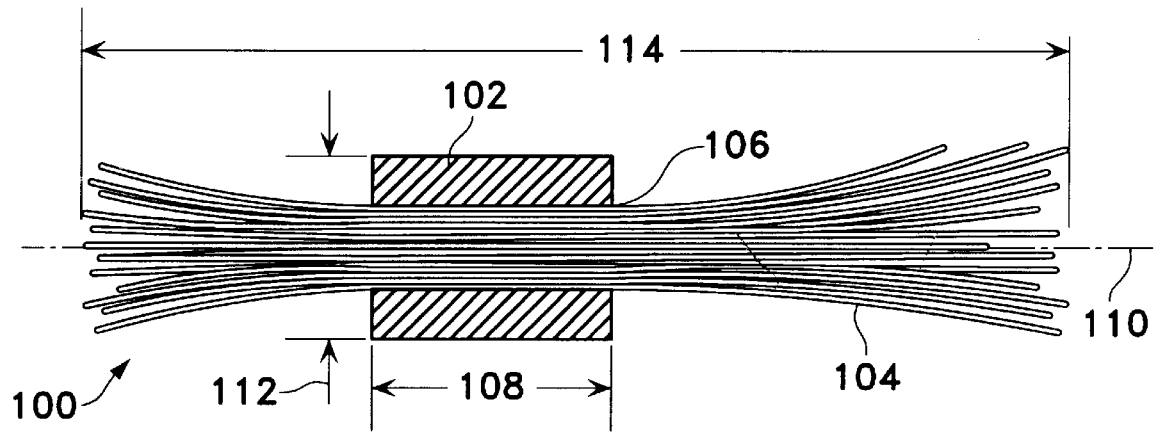
FIG. 1 is a side view of a generalized version of the inventive vaso-occlusive device showing the conventions used in describing various aspects of the invention.

FIG. 1 shows in cross section a side view of a generalization of the inventive vaso-occlusive device (100). FIG. 1 shows the convention and defines many of the specific terms used herein. The retainer or binder (102) is so-called because in most variations of the inventions it retains the included fiber bundle (104) located in the passageway (106) located in retainer (102). The retainer (102) has a retainer length (108) which extends along the retainer axis (110) between the furthermost ends of the retainer (102). Similarly, the retainer (102) has a diameter (112) which is the outer limit of the retainer (102) generally perpendicular to the axis (110). Most desirable to this invention are retainers (102) in which the ratio of retainer length (108) to diameter (112) is no more than about two, preferably no more than about one.

The fiber portion (104) of the device (100) is a multiplicity of fibers having a length (114) which reflects the longest fiber extension in a specific device (100). Preferable to this invention are those structures in which the ratio of the length (114) of the fibers to the retainer length (108) is at least two, more preferably at least five.

Although the size of the device (100) is dependent upon the specific use to which it is placed, for most endovascular uses, the diameter (112) of retainer (102) typically will be between 0.005 and 0.090 inches. Smaller sizes are desirable because of the intent to use those devices in small, distal arteries. For that indication, a retainer outside diameter (112) of 0.005 to 0.015 inches is preferred.

The length (114) of the fibers are typically in the range of 0.100 inches or more.

The device (100) is typically radio-opaque. Either or both of the retainer (102) and the fibers (104) may be radio-opaque. The retainer (102) may be made of any material suitable for holding onto the fibers. Typical materials include those metal or alloys selected from the group consisting of various stainless steels, gold, tungsten, platinum, palladium, rhodium, rhenium and alloys thereof. Preferred is an alloy of platinum and tungsten.

Other materials suitable for the retainer (102) include polymeric composition, e.g., adhesives and moldable caulks. Especially preferred are epoxies, urethane, and silicones. Highly desirable as adjuncts to these polymeric compositions are particulate radio-opaque fillers, e.g., powder tantalum, barium carbonate, bismuth oxide, barium sulfate, and the like.

The materials used in the fibers (104) may be thrombogenic material but typically are silk, cotton, polesters such as the Nylons and polyethylene terephthalate (e.g., DACRON), polyurethane, polyethylene, etc.

Figure 2:
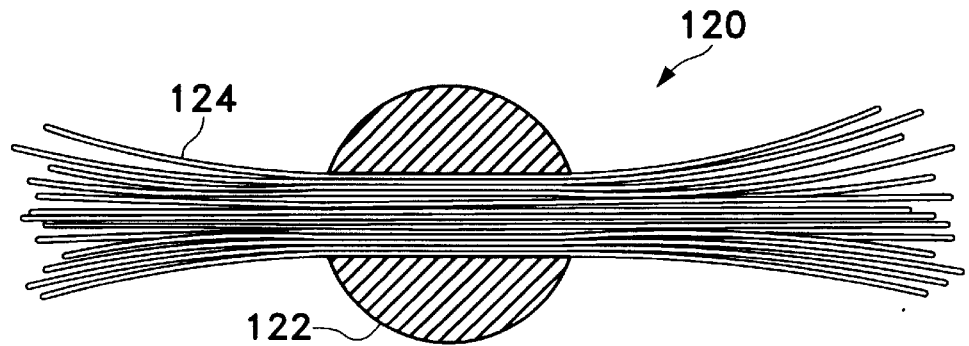
FIG. 2 shows a side cutaway view of a variation of the invention having a generally spherical binder.

FIG. 2 shows a side view, cross section of the inventive device (120) having a generally spherical retainer (122). In this variation, the passageway is an opening placed through the center of the retainer (122). The fibers (124) are held in place by, e.g., crimping or squeezing the retainer or by introducing a glue into the interior of the retainer. The fibers (124) are merely placed as tufts in the retainer (122).

Figure 3:
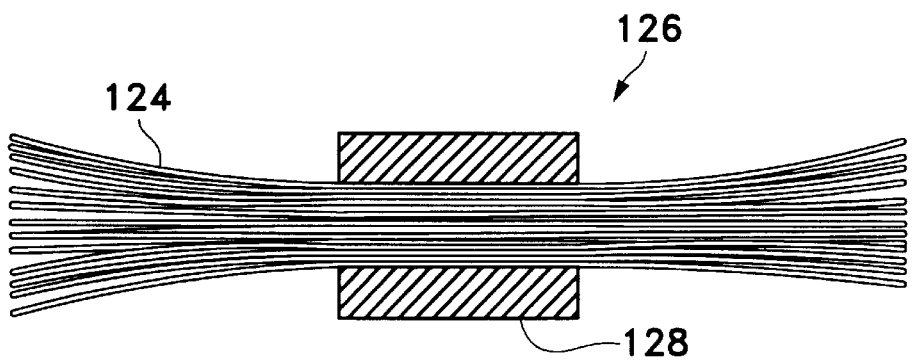
FIG. 3 shows a side cutaway view of a variation of the invention having a generally cylindrical binder.

FIG. 3 shows a side view cutaway of the device (126) in which the retainer (124) is generally cylindrical in shape. As was the case with the FIG. 2 variation, the fibers (124) pass through the center of the retainer (128)

Figure 4:
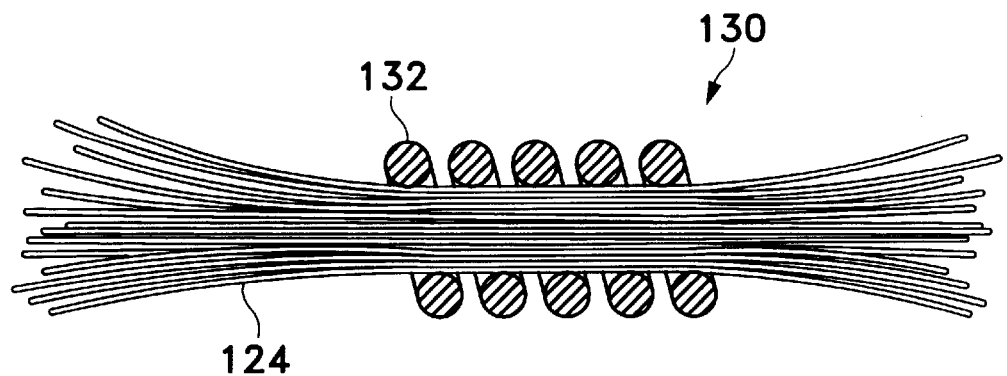
FIG. 4 shows a side cutaway view of a variation of the invention having a coil as a binder.

FIG. 4 shows a side view cutaway of a variation of the device (130) utilizing a coil as the retainer (132). When using high ductility metals in the coil retainer (132), it is sometimes desirable to augment the retainer (132) with a glue or the like to hold the fibers (124) with greater certainty.

Figure 5:
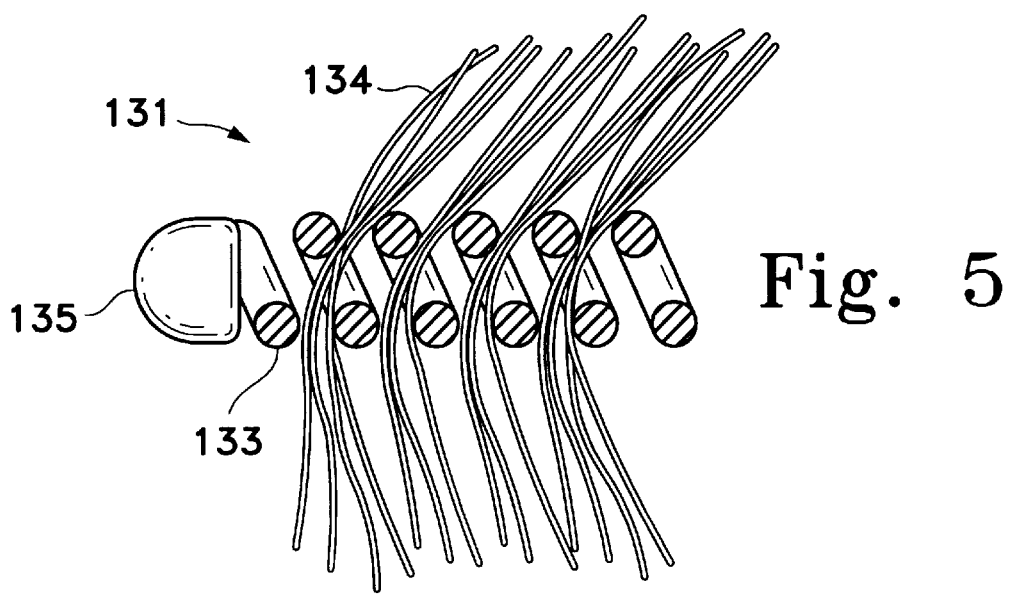
FIG. 5 shows a cutaway side view of a variation employing a coil retainer in which the fibers emanate from the side of the Retainer.

FIG. 5 shows a side view cutaway of a variation of the device (131) utilizing coil (133) as the retainer. In this variation of the device, the fibers (134) do not pass completely through the axis of the retainer coil (133). Instead they are pulled through and are held in place by the coil itself after insertion between turns of the coil. The length of the various fibers (134) are much longer than is the length of coil (133). Typical of the use of a coil such as this in which the leading edge of the coil is exposed to the lumen of a blood vessel is the use of a rounded tip (135) to the coil. Tip (135) may be made in a variety of different ways. The typical way of making such tip when the coil is of material which easily melts is simply to melt a portion of coil (133) to form the rounded tip on (135). Although the diameter of tip (135) is shown to be relatively the same as that of coil (133), the rounded tip may have a diameter which is larger or smaller than coil (133).

Figure 6:
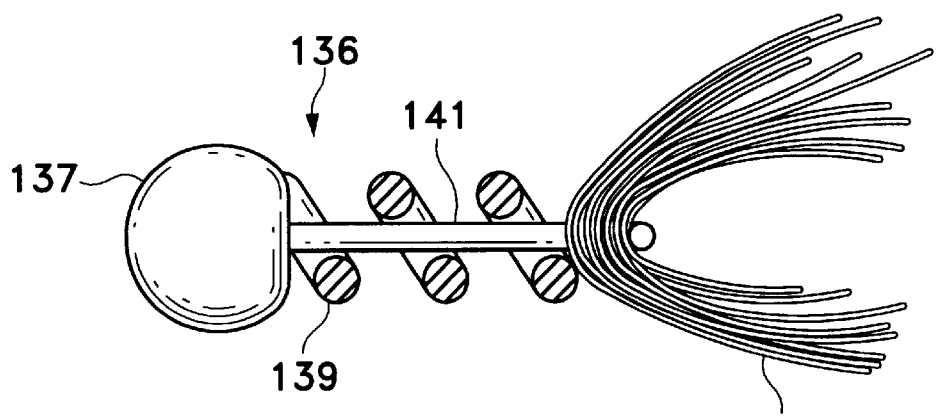
FIG. 6 shows a cutaway side view of a variation using a coil retainer and an interior clip to retain the thrombogenic fibers.

FIG. 6 shows still another variation of the vaso-occlusive device (136) utilizing a coil retainer (139). However, in this instance, the coil (139) is used only as a portion of a retainer assembly. The device which directly encloses the fibers (143) is a clip (141). The vaso-occlusive (136) additionally has rounded tip (137) as did the device shown in FIG. 5. This device might be assembled in the following manner: First, multiplicity of fibers (143) is included in an open u-shaped clip (141). The shank of the clip is then slid into the interior of coil (139) until the fibers fit snugly against the end of the coil opposite that portion where the head (137) is to be found. The end of the coil (139) is then heated or an amount of epoxy or the like is applied to form a rounded end (137). The rounded end (137), the coil (139), and the clip (141), all cooperate to hold fibers (143) in place.

Figure 7A:
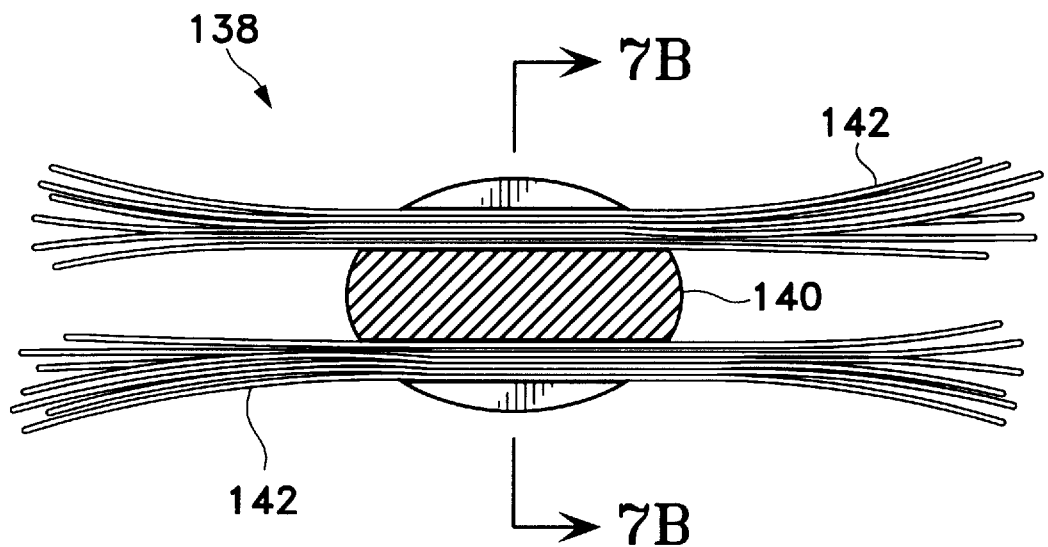
FIG. 7A shows a side view cutaway of a variation of the invention having a ovoid binder and having passageways for the fiber element through the binder.

FIG. 7A shows a side view, cutaway version of the inventive vaso-occlusive device (138) in which the retainer (140) is ovoid and the fibers (142) are introduced into a pair of passageways passing through the periphery of the retainer (140).

Figure 7B:
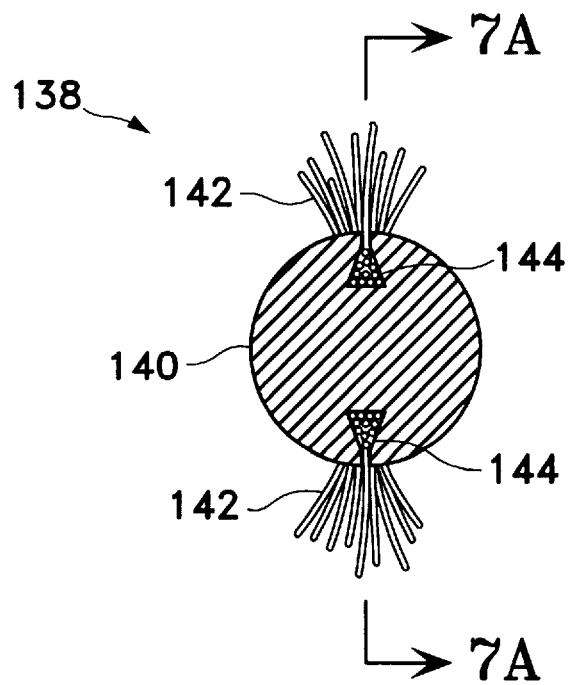
FIG. 7B is an end cutaway view of the FIG. 7A device.

FIG. 7B shows an end view of the FIG. 7A device (138) and shows the passageways (144 ) in the retainer (140). Although these passageways (144) are shown to be crimped or squeezed to hold the fibers (142) in place, it is acceptable to glue them in the external passageways (144). Passageways (144) are generally parallel to the axis of the retainer.

Figure 8A:
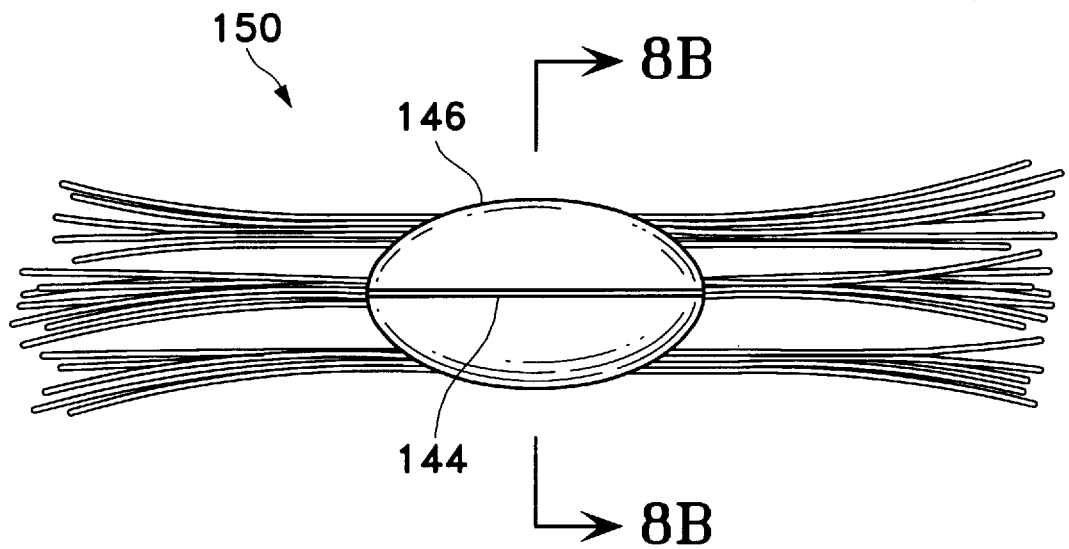
FIG. 8A is a side view of a device such as FIG. 7A but having multiple passageways.
Figure 8B:
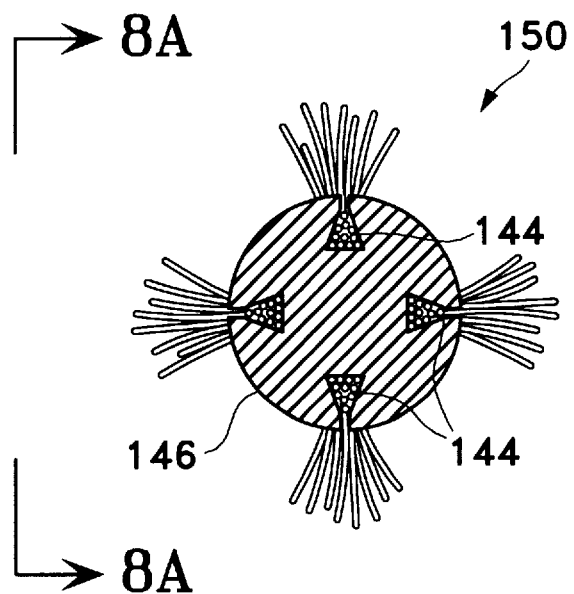
FIG. 8B is an end view of the FIG. 8A device.

FIG. 8A and 8B show variation (150) of the device shown in FIGS. 7A an 7B. The difference is the multiple number of passageways (144) in the retainer (146).

Figure 9A:
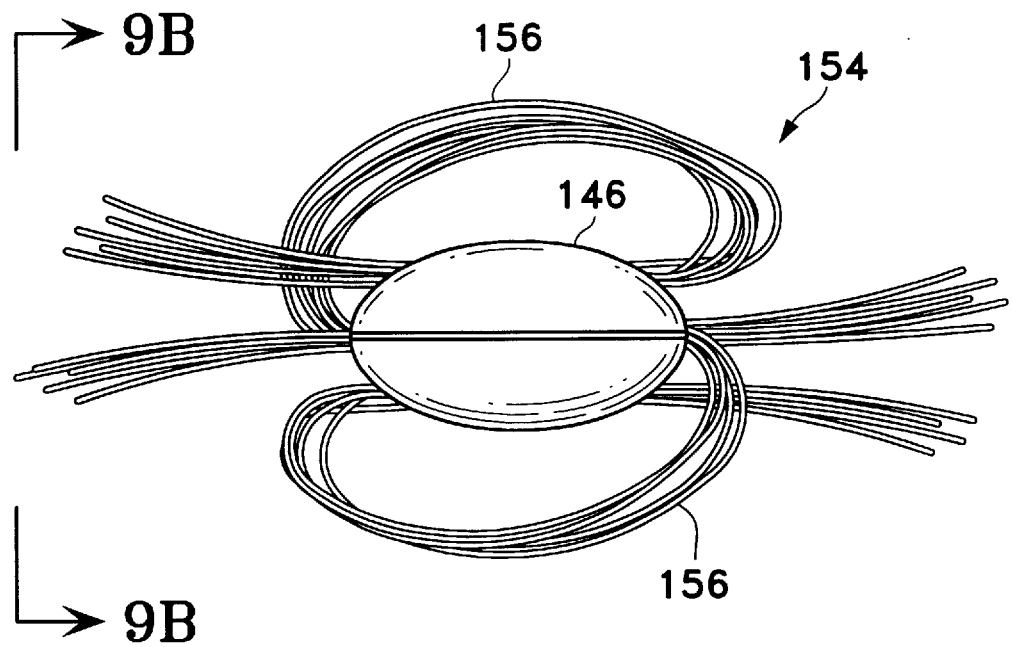
FIG. 9A is a side view of a variation of the invention having multiple passageways through the binder and loops of the fibers through these passageways.
Figure 9B:
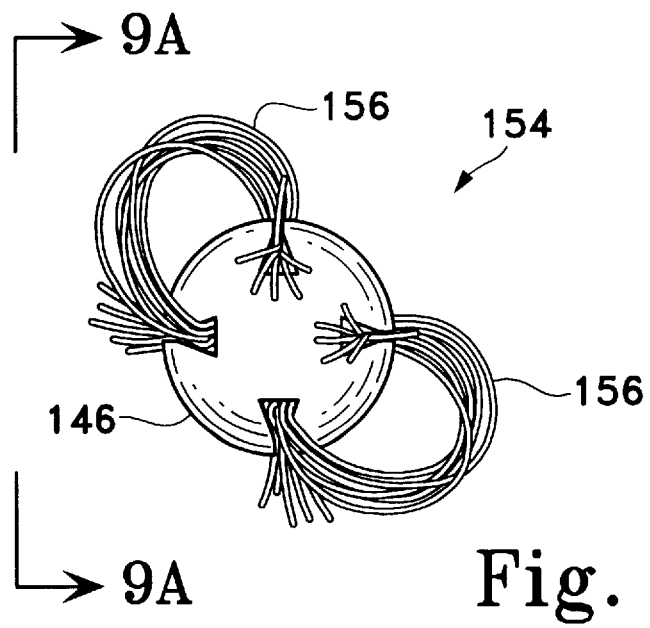
FIG. 9B is an end cutaway view of the FIG. 9A device.

FIGS. 9A and 9B show a variation of the device shown in FIGS. 8A and 8B. This device (154) uses the multiple passageway (144) retainer (146) portrayed in FIGS. 8A and 8B. Two bundles of fiber (156) are used. Each bundle (156) is routed through a first passageway (144) and looped around externally and then through an adjacent passageway.

This variation gives a larger overall effective diameter to the device (154) with enhanced thrombogenic area.

Figure 10:
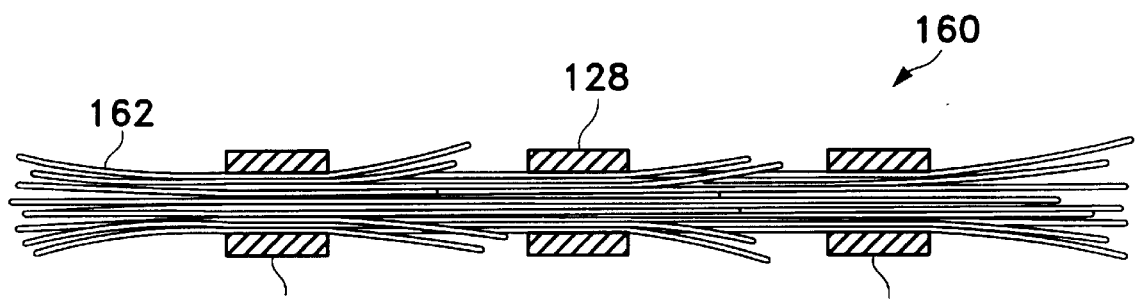
FIG. 10 is a side cutaway view of a multiple binder inventive device in which the fibers extend radially in the region between the binders.

FIG. 10 shows a longer variation (160) of the inventive device having multiple retainers (128). The fibers (162) are sized and situated in such a way that a portion of the bundle terminates between a pair of retainers (128). This variation (160) has the benefits of potentially shielding the retainer (128) from the interior of the delivery catheters during that delivery. It also provides for enhanced thrombogenicity.

Figure 11:
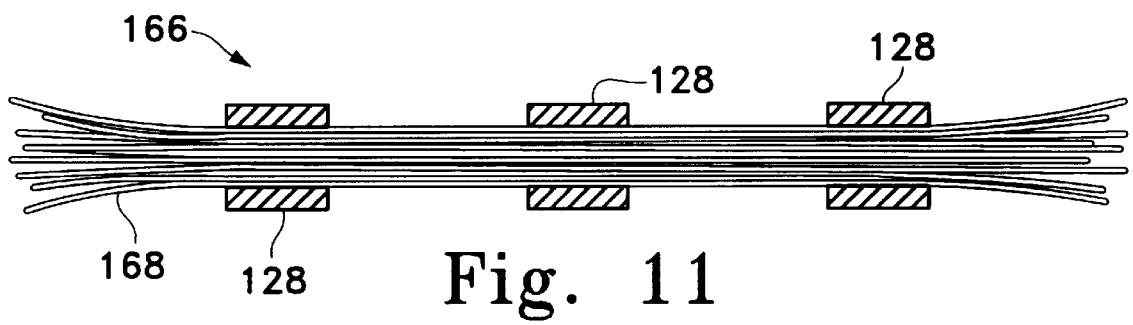
FIG. 11 is a side cutaway view of a multiple binder inventive device.

FIG. 11 shows a variation of the inventive vaso-occlusive device (166) in which multiple retainer (128) are used to hold the fiber bundle (168) in a straight through passage.

In the variation shown in FIGS. 10 and 11 and in the other multiple retainer variations, and of the retainers, e.g., ovoid, spherical, coil, cylindrical, may be used and they may be mixed, as is discussed below.

Figure 12:
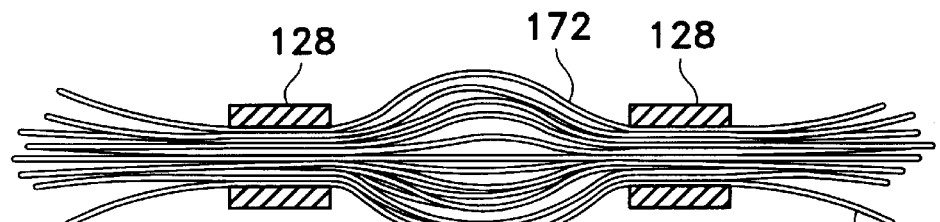
FIG. 12 show a side cutaway view of a multiple mixed binder device with folded fibers encompassing an end binder.

FIG. 12 shows a multiple retainer (128) variation of the devices (170) in which the outer fibers (172) in the bundle (174) extend outwardly past the outer diameter of the retainer (128). The center fibers in the bundle (174) are straight in this configuration.

Figure 13:
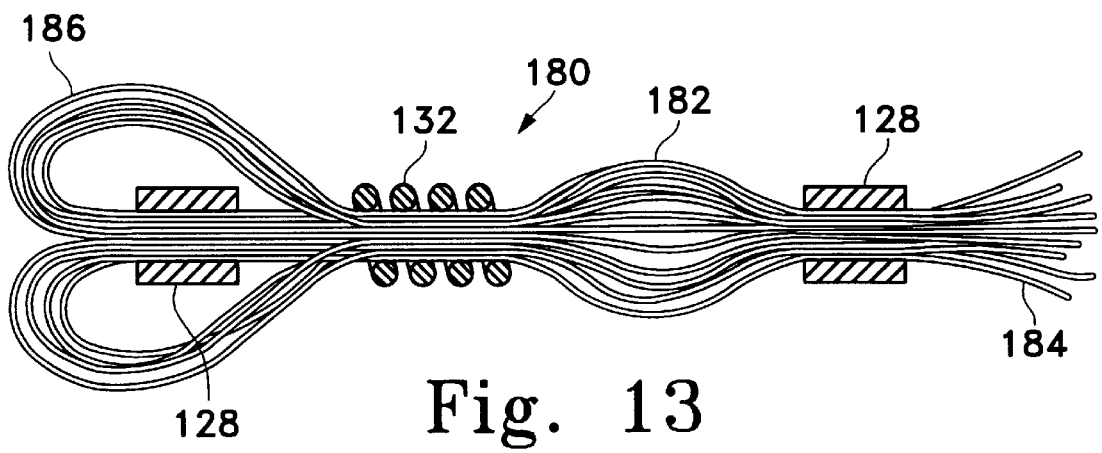
FIG. 13 is a view of a multiple binder Inventive Device.

FIG. 13 shows another multiple retainer configuration (180) of the device. The retainers are a mixture of cylinder (128) and a coil (132). In this variation, the outer fibers (182) of the bundle (184) extend outwardly between the binders (128, 132). The fiber bundle (184) is also folded back over itself at the end (186) and passed back through one of the binders (132). This variation of the invention provides a large leading hydraulic surface to the device when introducing the device using fluid pressure delivery.

This device may be delivered using typical pusher techniques and an endovascular catheter as described in the Ritchart et al. patent or using the hydraulic techniques described in U.S. patent application Ser. No. 07/978,320, filed Oct. 9, 1992, to Zenzen et al.

This invention has been described using examples of the preferred embodiments. Obvious variations of the invention within the equivalents of the invention found in the following claims are considered to be within the scope of the invention.

We claim as our invention:

1. A vaso-occlusive device comprising:
    a) at least one retainer having opposing ends, a retainer axis extending between those ends, an axial length, at least one passageway extending along said axis; and
    b) a multiplicity of fibers fixedly attached to said retainer and said multiplicity of fibers having a fiber length extending beyond the retainer axial length, passing through and substantially filling said at least one passageway reflecting the longest fiber extension beyond said retainer ends and wherein the ratio of said fiber length to the retainer axial length is at least two.

2. The device of claim 1 wherein the retainer has a retainer diameter and wherein the retainer diameter is such that the ratio of the retainer axial length to the retainer diameter is no more than two.

3. The device of claim 1 wherein the retainer is radio-opaque.

4. The device of claim 1 wherein the retainer comprises a material selected from the group consisting of stainless steel, gold, tungsten, platinum, palladium, rhodium, rhenium, and alloys thereof.

5. The device of claim 1 wherein the retainer comprises a polymeric material.

6. The device of claim 5 wherein the polymeric material comprises an epoxy.

7. The device of claim 1 wherein the retainer has a shape selected from spheroid, ovoid, and cylindrical.

8. The device of claim 1 wherein the retainer comprises a coil.

9. The device of claim 1 wherein the device comprises a multiplicity of retainers.

10. The device of claim 9 wherein a portion of the fibers terminate between at least two of said multiplicity of retainers.

11. The devices of claim 9 wherein the multiplicity of fibers extend outwardly from the retainer axis between said at least two of said multiplicity of retainers.

12. The device of claim 9 wherein at least a portion of said multiplicity of fibers pass through said at least one retainer twice.

13. A vaso-occlusive device comprising:
    a) at least one helical retainer coil having opposing ends, a retainer axis between those ends, a retainer axial length, a retainer passageway extending along said axis;
    b) a clip having a closed end and arms extending from that closed end, wherein the arms are passed through the retainer passageway from one opposing end to the other, and
    c) a multiplicity of fibers fixedly attached to said retainer and said multiplicity of fibers passing through the closed end of the clip having a maximum fiber length, wherein the length of maximum fiber length is such that the value of the ratio of the maximum fiber length to the retainer axial length is at least two.

14. The device of claim 13 wherein the clip is held in place within the retainer coil by a rounded end located at the end of the retainer coil opposite the coil end adjacent the fibers.

15. The device of claim 13 wherein the helical retainer coil has a retainer diameter and wherein the retainer diameter is such that the value of the ratio of the retainer axial length to the retainer diameter is no more than two.

16. The device of claim 13 wherein the retainer is radio-opaque.

17. The device of claim 13 wherein the retainer coil comprises a material selected from the group consisting of stainless steel, gold, tungsten, platinum, palladium, rhodium, rhenium and alloys thereof.

* * * * *

UNITED STATES PATENT AND TRADEMARK OFFICE
CERTIFICATE OF CORRECTION

PATENT NO. : 5,843,118
DATED : December 1, 1998
INVENTOR(S) : Sepetka et al.

It is certified that error appears in the above-identified patent and that said Letters Patent is hereby corrected as shown below:

In the Claims:

Claim 1a) should read:

a) at least one retainer ending in terminating opposing ends, a retainer axis extending between those ends, a retainer axial length, at least one passageway extending along said axis; and Signed and Sealed this Twenty-seventh Day of July, 1999

Attest:

Q. TODD DICKINSON

Attesting Officer

Acting Commissioner of Patents and Trademarks